United States Patent
Sukumar et al.

(10) Patent No.: US 10,836,693 B2
(45) Date of Patent: Nov. 17, 2020

(54) PROCESS FOR THE PREPARATION OF DOCOSANOL

(71) Applicants: Nandi Sukumar, Hyderabad (IN); Theriviam Sudalayandi Shanmugam Sundaram Dhanraj, Hyderabad (IN); Sreedhar Reddy Dwarakapally, Hyderabad (IN); Ravi Kumar Gupta Miriyala, Hyderabad (IN); Sivakumaran Meenakshisunderam, Hyderabad (IN)

(72) Inventors: Nandi Sukumar, Hyderabad (IN); Theriviam Sudalayandi Shanmugam Sundaram Dhanraj, Hyderabad (IN); Sreedhar Reddy Dwarakapally, Hyderabad (IN); Ravi Kumar Gupta Miriyala, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 0 days.

(21) Appl. No.: 16/475,087

(22) PCT Filed: May 28, 2018

(86) PCT No.: PCT/IB2018/053770
§ 371 (c)(1),
(2) Date: Jun. 29, 2019

(87) PCT Pub. No.: WO2018/220504
PCT Pub. Date: Dec. 6, 2018

(65) Prior Publication Data
US 2019/0330131 A1    Oct. 31, 2019

(30) Foreign Application Priority Data

May 30, 2017 (IN) .............................. 201741018965

(51) Int. Cl.
*C07C 31/125* (2006.01)
*C07C 29/147* (2006.01)

(52) U.S. Cl.
CPC .......... *C07C 29/147* (2013.01); *C07C 31/125* (2013.01); *C07B 2200/13* (2013.01)

(58) Field of Classification Search
USPC ........................................................ 568/885
See application file for complete search history.

(56) References Cited

PUBLICATIONS

Tanaka et al. Bulletin of the Institute for Chemical Research, Kyoto University (1959), 37, 281-93.*
Katz et al., Proc. Natl. Acad. Sci., 1991, vol. 88, pp. 10825-10829.*
Pubchem—Docosanol, Sep. 16, 2004, p. 1-58.*

* cited by examiner

*Primary Examiner* — Ana Z Muresan
(74) *Attorney, Agent, or Firm* — Jay R Akhave

(57) ABSTRACT

The present invention provides a process for the preparation of Docosanol (I). The process comprises reducing cis-13-Docosenoic acid (V) to obtain Docosanoic acid (III), which is further reduced to obtain Docosanol (I).

Formula I

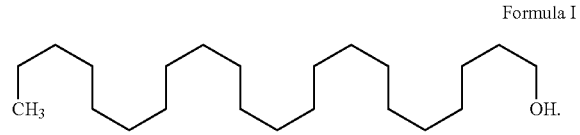

6 Claims, 1 Drawing Sheet

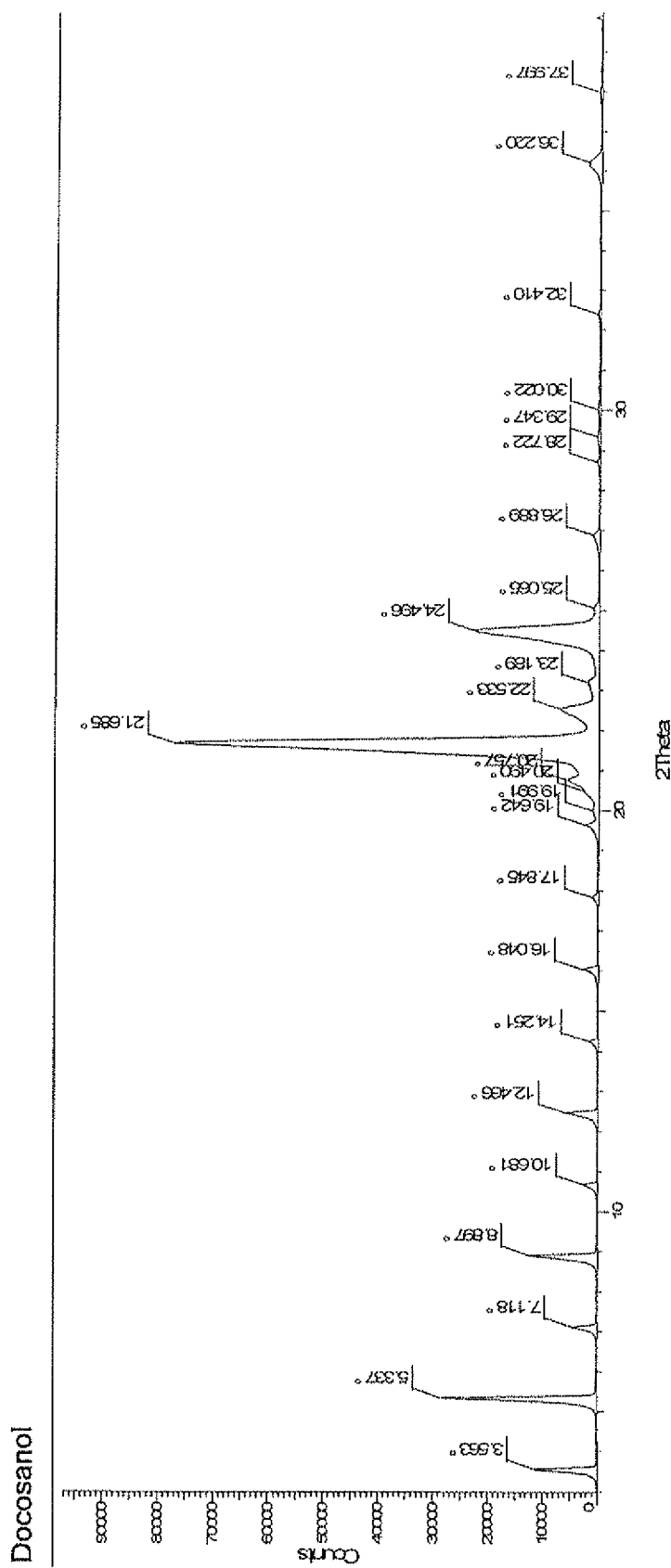

PROCESS FOR THE PREPARATION OF DOCOSANOL

FIELD OF INVENTION

The present invention relates to a process for the preparation of Docosanol of Formula I.

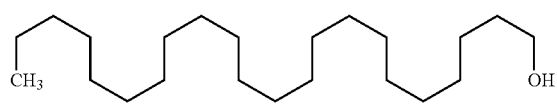

Formula I

BACKGROUND OF THE INVENTION

Docosanol (I) is chemically known as Behenyl alcohol or n-Docosanol. It is used as antiviral agent for reducing the duration of cold sores caused by the herpes simplex virus. Docosanol (I) is being marketed in the US under the brand name Abreva® as topical cream.

Indian Journal of Chemistry, 1996, 35B, 1239 discloses a process for preparing Docosanol (I) involves, catalytic reduction of 6-docosenoic acid (II) using $Pd/C/H_2$ to produce docosanoic acid (III), which is esterified with MeOH to produce methyl docosanoate (IV). The compound (IV) is reduced using Lithium aluminium hydride ($LiAlH_4$) to produce Docosanol (I).

The process is as shown in scheme-I below:

Scheme-I

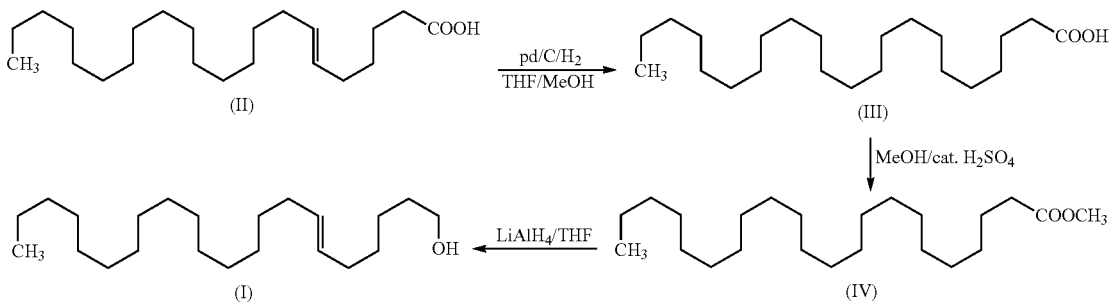

The major drawback associated with the above process is more number of steps, usage of 6-docosenoic acid as a key raw material, which is not a commercially/readily available raw material for large scale manufacturing. Furthermore, the usage of Lithium aluminium hydride ($LiAlH_4$) for reduction, which is a costly and pyrophoric reagent, requires special attention during large scale of production.

Journal of Biological chemistry, 1924, 59, 905 discloses a process for the preparation of Docosanol (I) involves, esterification of cis-13-docosenoic acid (Erucic acid) (V) with MeOH or EtOH to produce methyl or ethyl docosenoate (VI), which is reduced with colloidal palladium to produce docosanoic acid (III). The compound (III) is further reduced with Na metal to produce Docosanol (I).

The process is as shown in scheme-II below:

Scheme-II

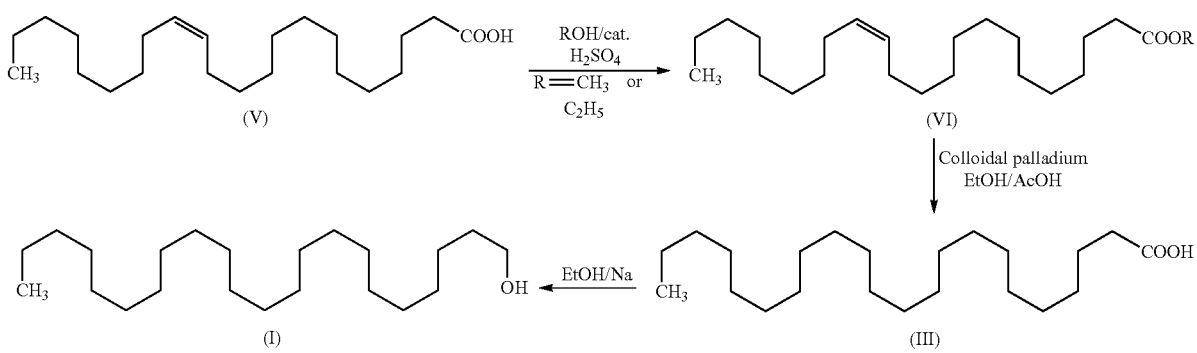

The main disadvantage of the above process is the usage of colloidal palladium and metallic sodium, which is difficult to operate in large scale.

Similarly like above processes, U.S. Pat. No. 4,186,211, CN 1796346 and Indian journal of chemistry, 2002, 41B, 1724 discloses process for the preparation of Docosanol (I) by reducing Docosanoic acid (III) using Lithium aluminium hydride (LiAlH$_4$). However, there is always a need for alternative preparative routes, which for example, involve fewer steps, usage of reagents that are less expensive and/or easier to handle and raw materials which are readily/commercially available.

Hence, there is a need to develop cost effective and commercially viable process involves minimum number of steps for the preparation of Docosanol of Formula (I).

The present invention is directed towards a process for the preparation of Docosanol of Formula (I) involves, catalytic reduction of cis-13-docosenoic acid (V) to obtain Docosanoic acid (III), which is further reduced to obtain Docosanol (I).

Objective of Invention

The main objective of the present invention is to provide a simple and cost effective process for the preparation of Docosanol (I) which is industrially viable.

SUMMARY OF THE INVENTION

The present invention provides a crystalline Form of Docosanol (I), which is characterized by X-ray diffraction spectrum and shows peaks at the diffraction angles of about 3.5, 5.3, 7.1, 8.8, 10.6, 12.4, 14.2, 17.8, 19.6, 19.9, 20.4, 21.6, 22.5, 23.1, 24.4, 25.0, 26.8, 28.7, 32.4, 36.2°±0.2° two theta, substantially as shown in FIG. 1.

In another embodiment, the present invention is to provide a process for the preparation of Docosanol of Formula (I).

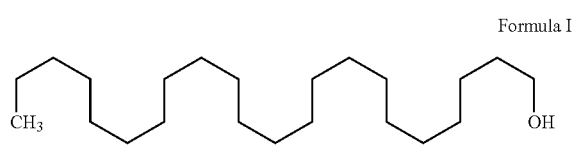 [SMILES: CCCCCCCCCCCCCCCCCCCCCCO]

Formula I which comprises:
(i) reducing cis-13-docosenoic acid (V),

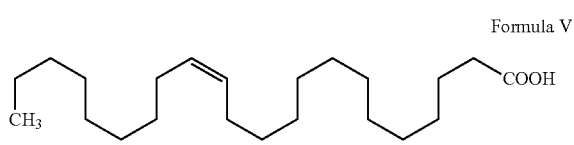 [SMILES: CCCCCCCC/C=C\CCCCCCCCCCCC(=O)O]

Formula V to obtain Docosanoic acid (III),

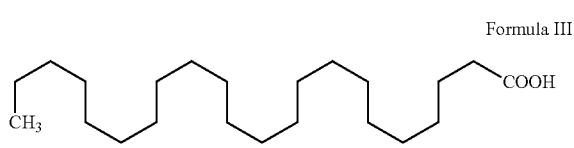 [SMILES: CCCCCCCCCCCCCCCCCCCCCC(=O)O]

Formula III (ii) reducing Docosanoic acid (III) to obtain Docosanol (I).

In another embodiment, the present invention is to provide an improved process for the preparation of Docosanol of Formula (I) comprises,
(i) reducing Docosanoic acid (III),
(ii) isolating Docosanol (I).

BRIEF DESCRIPTION OF THE DRAWINGS

FIG. 1 Illustrates the X-ray powder diffraction pattern of crystalline Form of Docosanol produced by the present invention.

BRIEF DESCRIPTION OF ABBREVIATIONS

NaBH$_4$— Sodium borohydride
I$_2$— Iodine
CF$_3$COOH— Trifluoroacetic acid
KBH$_4$— Potassium borohydride
HfCl$_4$— Hafnium tetrachloride
Br$_2$— Bromine
CNCl—Cyanogen chloride
LiCl-Lithium chloride
BF$_3$— Boron trifluoride
ZnCl$_2$—Zinc chloride
CaCl$_2$— Calcium chloride
AlCl$_3$— Aluminum trichloride
TiCl$_4$— Titanium tetrachloride
ZrCl$_4$— Zirconium tetrachloride
KBH$_4$— Potassium tetrahydroborate
MgCl$_2$— Magnesium chloride
PPh$_3$—Triphenylphosphine
DMF—Dimethylformamide
THF—Tetrahydrofuran

DETAILED DESCRIPTION OF THE INVENTION

The present invention provides a crystalline Form of Docosanol, which is characterized by X-ray diffraction pattern with peaks at about 3.5, 5.3, 7.1, 8.8, 10.6, 12.4, 14.2, 17.8, 19.6, 19.9, 20.4, 21.6, 22.5, 23.1, 24.4, 25.0, 26.8, 28.7, 32.4, 36.2°±0.2° two theta, substantially as shown in FIG. 1.

In another embodiment, the present invention is to provide an improved process for the preparation of Docosanol of Formula (I).

The process comprises, cis-13-docosenoic acid (V) is hydrogenated in presence of metal catalyst to obtain Docosanoic acid (III).

The metal catalyst used in the above reaction comprises palladium-on-carbon (Pd/C), Tetrakis(triphenylphosphine) palladium(0), nickel nanoparticles immobilized on hierarchical zeolite, platinum(IV) oxide, iron in acidic media such as acetic acid, formic acid, hydrochloric acid, hydrobromic acid and the like; sodium hydrosulfite, sodium sulfide, tin(II) chloride, titanium(III) chloride, zinc, rhodium, ruthenium and nickel catalysts such as raney nickel or urushibara nickel.

The above reaction is carried out in the presence of a solvent. The solvent comprises an alcohol selected from C$_1$-C$_{10}$ straight or branched chain alcohol such as methanol, ethanol, isopropyl alcohol, 1-butanol, 2-butanol, 2-methyl-2-propanol, 1-pentanol, 2-pentanol, 2,2-dimethyl-1-propanol, 2,2,2-trimethyl ethanol, 1-decanol, benzyl alcohol; hydrocarbon solvent selected from the group toluene, benzene, o-xylene, m-xylene, p-xylene; water; acetone; acetonitrile; ethyl acetate; methylene chloride; DMF; dioxane, THF or mixture thereof.

The compound (III) is isolated as a solid or as such used in next step. Optionally, Compound (III) is subjected to purification either by column chromatography or by crystallization.

Still another embodiment of the present invention is Docosanoic acid (III) is further reduced to obtain Docosanol (I).

The reducing agent used in the above reaction comprises boron compound and an activation agent comprises $NaBH_4/I_2$, diborane, $NaBH_4$/Catechol/$CF_3COOH$, $NaBH_4$/Acetic acid, $NaBH_4/CF_3COOH$, $NaBH_4$/Sulfuric acid, $NaBH_4$/cyanuric acid, $NaBH_4$/Cyanuric halide, $KBH_4/HfCl_4$, $NaBH_4/HfCl_4$, $NaBH_4$/MeOH, $NaBH_4/Br_2$, $NaBH_4/(CNCl)_3$, $NaBH_4/LiCl$, $NaBH_4/BF_3$ etherate, $NaBH_4/ZnCl_2$, $NaBH_4/CaCl_2$, $NaBH_4/AlCl_3$, $NaBH_4/TiCl_4$, $NaBH_4/ZrCl_4$, $KBH_4/LiCl$, $KBH_4/ZnCl_2$, $KBH_4/MgCl_2$, $NaBH_4$/2,4,6-Trichloro[1,3,5]triazine/$PPh_3$, $NaBH_4$/TCT (2,4,6-Trichloro[1,3,5]triazine)/NMM (N-methylmorpholine), $NaBH_4$/CDI (Carbonyldiimidazole), $NaBH_4$/BOP reagent ((Benzotriazol-1-yloxy)tris(dimethylamino) phosphonium hexafluorophosphate), $NaBH_4$/Sulfonylbenzotriazole derivatives, $NaBH_4$/3,4,5-trifluorophenylboronic acids, $NaBH_4$/1-propanephosphonic acid cyclic anhydride and the like.

The above reaction is carried out in the presence/absence of a solvent. The solvent comprises an ether selected as tetrahydrofuran, dioxane, diisopropylether, diethylether, 2-methyltetrahydrofuran, cyclopentyl methyl ether, methyl tert-butyl ether, diglyme or monoglyme; an alcohol selected from $C_1$-$C_{10}$ straight or branched chain alcohol such as methanol, ethanol, isopropyl alcohol, 1-butanol, 2-butanol, 2-methyl-2-propanol, 1-pentanol, 2-pentanol, 2,2-dimethyl-1-propanol, 2,2,2-trimethyl ethanol, 1-decanol, benzyl alcohol; hydrocarbon solvent selected from the group toluene, benzene, o-xylene, m-xylene, p-xylene; water; acetone; acetonitrile; ethyl acetate; methylene chloride; DMF; an aliphatic hydrocarbon selected from $C_{1-8}$ carbon atoms containing straight chain or branched chain or cycloalkane substituted cycloalkane or mixture thereof.

The Docosanol (I) is isolated as a solid. Optionally, Compound (I) is subjected to purification either by column chromatography or by crystallization by known methods, for example by dissolving in a solvent comprises, methanol, ethanol, propanol, isopropanol, ethyl acetate, methylene chloride, hexane, heptane, cyclohexane, acetone, THF, acetonitrile, methyl-tert-butyl ether, diisopropyl ether, diethyl ether, water or mixtures thereof; and precipitating pure compound by cooling the solution or by adding an anti solvent comprises, cyclohexane, n-hexane, n-heptane, water etc.

The following example(s) illustrate the nature of the invention and are provided for illustrative purposes only and should not be construed to limit the scope of the invention.

EXAMPLE-1

Preparation of Docosanoic Acid:

13-Docosenoic acid (100 g) was suspended in THF (1500 ml) at 20-30° C. and hydrogenated in the presence of Palladium on charcoal (5 g, 10% w/w, 50% wet) at 20-30° C. over a hydrogen pressure of 6-8 Kg/cm². After completion of reaction the catalyst was filtered off, solvent was evaporated from the filtrate under reduced pressure (20-40 mm Hg) at 40-50° C. to get a white colour residue. The above residue was suspended in methanol (1000 ml) and heated to 60-65° C. to obtain a clear solution and cooled to 20-30° C. slowly over a period of 30±5 min stirred for an hour at 20-30° C. The resulting solid was filtered and dried under reduced pressure (10-20 mm Hg) at 40-45° C. to afford 90.83 g of Docosanoic acid.

Yield: 90.3% of theory
Chromatographic purity (by GC): >98%

EXAMPLE-2

Preparation of Docosanol:

Sodium borohydride (2.9 g) was suspended in THF (100 ml) at 20-30° C. and cooled to 0-5° C. Thereafter, added a solution of iodine (7.5 g) dissolved in THF (30 ml) over a period of 1-2 h at 0-5° C. followed by a solution of docosanoic acid (20 g) dissolved in THF (140 ml) in 30-40 min. The reaction mixture was stirred for 2-4 h at 20-30° C. After completion of reaction, the reaction mixture was carefully quenched with dil. HCl (30 ml, 3N) at 20-30° C. and evaporated the solvent under reduced pressure (40-50 mm Hg) at 40-45° C. to get a turbid oily mass. To the above residue DM water (200 ml) was added and extracted the product in methyl-tert-butyl ether (300 ml). The organic extract was washed with an aqueous solution of 10% w/w sodium hydroxide (100 ml), an aqueous solution of 5% w/w sodium metabisulfite and finally with DM water (100 ml). Thereafter, the organic extract was concentrated under reduced pressure (20-40 mm Hg) at 40-50° C. to get a white colour residue. The above residue was dissolved in n-heptane (100 ml) at 40-45° C. and stirred for an hour at 20-25° C. The resulting solid was filtered and dried under reduced pressure (10-20 mm Hg) to afford 16.8 g of the title compound.

Yield: 87.6% of theory
Chromatographic purity (by GC): >98%

EXAMPLE-3

Preparation of Docosanol:

Sodium borohydride (22.3 g) was suspended in tetrahydrofuran (500 ml) at 25-30° C. and cooled to 0-5° C. A solution of Docosanoic acid (100 g) dissolved in tetrahydrofuran (1.0 Lt) was added slowly over a period of 30±5 min at 0-5° C. Borontrifluoride diethyletherate (104.0 g) was added slowly to above reaction mixture in 30±5 min at 0-5° C. The reaction mixture was stirred at 20-30° C. and the progress of the reaction was monitored by qualitative HPLC analysis. The above reaction mass was cooled to 0-5° C. and DM water (200 ml) was added slowly over a period of 30±5 min at 0-5° C. The reaction mixture was stirred at 20-30° C. for 30±5 min, and then concentrated under reduced pressure (~20 mm Hg) at 40-45° C. The concentrated mass was cooled to 20-30° C. and methyl-tert-butyl ether (2.0 Lt) was added. To the reaction mass 10% w/w aqueous sodium hydroxide solution [1.0 Lt, prepared by dissolving sodium hydroxide (100 g) in DM water (1.0 Lt)] was added at 20-30° C. The reaction mass was stirred at 35-40° C. for 30±5. Methyl-tert-butyl ether layer was separated at 35-40° C., washed with DM water (2×1.0 Lt) at 35-40° C., filtered through hyflo bed at 35-40° C. and washed with methyl-tert-butyl ether (2×10 ml, 20-30° C.). The organic layer was concentrated under reduced pressure (~20 mm Hg) at a temperature below 45° C. Ethyl acetate (500 ml) was added to the concentrated mass at 40-50° C. The reaction contents were heated to 50-55° C. to obtain a clear solution and cooled to 20-30° C. slowly over a period of 30±5 min. The reaction suspension was stirred for 1 h±10 min at 20-30° C.

The precipitated product was filtered and washed with ethyl acetate (2×50 ml, 20-30° C.). The wet filtered mass was suspended in ethyl acetate (500 ml) at 20-30° C. and heated to 50-55° C. to obtain a clear solution. The resulted solution was cooled to 20-30° C. slowly over a period of 30±5 min. The reaction suspension was stirred for 1 h±10 min at 20-30° C. for complete product precipitation. The product was filtered and washed with ethyl acetate (2×50 nil, 20-30° C.). The wet product was dried under reduced pressure (~20 mm Hg).

Yield: 82% of theory
Chromatographic purity (by GC): 99.9%

We claim:

1. A crystalline Form of Docosanol (I),

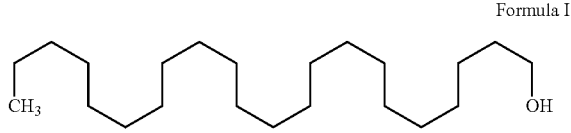

Formula I which is characterized by X-ray diffraction pattern with peaks at about 3.5, 5.3, 7.1, 8.8, 10.6, 12.4, 14.2, 17.8, 19.6, 19.9, 20.4, 21.6, 22.5, 23.1, 24.4, 25.0, 26.8, 28.7, 32.4, 36.2°±0.2° two theta as shown in FIG. 1; wherein Docosanol of Formula I having purity >99.5%.

2. A process for the preparation of Docosanol of Formula (I) having purity >99.5% of claim 1,

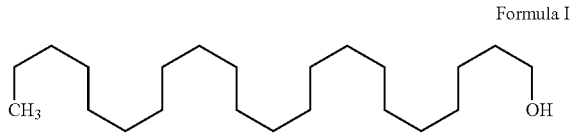 [SMILES: CCCCCCCCCCCCCCCCCCCCCCO]

Formula I which process comprises:
(i) reducing cis-13-docosenoic acid of formula (V),

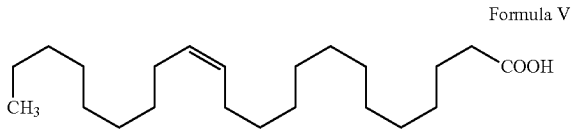 [SMILES: CCCCCCCC/C=C\CCCCCCCCCCCC(=O)O]

Formula V to obtain Docosanoic acid of formula (III),

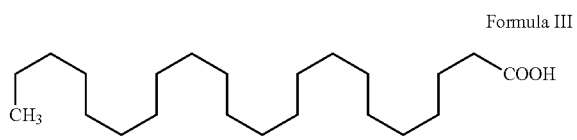 [SMILES: CCCCCCCCCCCCCCCCCCCCCC(=O)O]

Formula III (ii) reducing Docosanoic acid of formula (III) to obtain Docosanol of formula (I).

3. The process as claimed in claim 2, wherein the reaction of step (i) is carried out in presence of a metal catalyst selected from the group consisting of palladium-on-carbon (Pd/C), Tetrakis(triphenylphosphine)palladium(0), nickel nanoparticles immobilized on hierarchical zeolite, platinum (IV) oxide, iron in acidic media selected from the group consisting of acetic acid, formic acid, hydrochloric acid, hydrobromic acid; sodium hydrosulfite, sodium sulfide, tin (II) chloride, titanium(III) chloride, zinc, rhodium, ruthenium and nickel catalysts selected from the group consisting of raney nickel or urushibara nickel.

4. The process as claimed in claim 2, wherein the reaction of step (i) is carried out in presence of a solvent selected from the group consisting of $C_1$-$C_{10}$ straight or branched chain alcohol selected from the group of consisting of methanol, ethanol, isopropyl alcohol, 1-butanol, 2-butanol; hydrocarbon solvent selected from the group consisting of toluene, benzene, o-xylene, m-xylene, p-xylene; water; acetone; acetonitrile; ethyl acetate; methylene chloride; DMF; dioxane, THF; ether solvent selected from the group of consisting of diethyl ether, cyclopentyl methyl ether, MTBE or mixture thereof.

5. The process as claimed in claim 2, wherein the reaction of step (ii) is carried out in the presence of reducing agent selected from the group consisting of $NaBH_4$/$I_2$, diborane, $NaBH_4$/Catechol/$CF_3COOH$, $NaBH_4$/Acetic acid, $NaBH_4$/$CF_3COOH$, $NaBH_4$/$BF_3$ etherate, $NaBH_4$/Sulfuric acid, $NaBH_4$/cyanuric acid, $NaBH_4$/Cyanuric halide, $KBH_4$/$HfCl_4$, $NaBH_4$/$HfCl_4$, $NaBH_4$/3,4,5-trifluorophenylboronic acids, and $NaBH_4$/1-propanephosphonic acid cyclic anhydride.

6. The process as claimed in claim 2, wherein the reaction is carried out in absence of a solvent.

\* \* \* \* \*